US006358514B1

(12) United States Patent
Boussouira et al.

(10) Patent No.: US 6,358,514 B1
(45) Date of Patent: Mar. 19, 2002

(54) COMBINATION OF A RETINOID WITH A HISTIDINE DERIVATIVE

(75) Inventors: Boudiaf Boussouira, Paris; Michel Philippe, Wissous, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/317,859

(22) Filed: May 25, 1999

(30) Foreign Application Priority Data

May 26, 1998 (FR) ............................. 98 06603

(51) Int. Cl.⁷ ........................... A61K 6/00; A61K 7/00; A61K 7/42; A61K 7/135; A61K 7/021; A61K 7/025; A61K 9/14; A61K 9/127

(52) U.S. Cl. ........................... 424/401; 424/59; 424/62; 424/63; 424/64; 424/70.1; 424/70.9; 424/70.27; 424/450; 424/489

(58) Field of Search ............................. 424/59, 63, 64, 424/70.1, 70.9, 400, 401, 450, 489, 62, 70.27

(56) References Cited

U.S. PATENT DOCUMENTS

| 3,929,840 A | * 12/1975 | Christensen et al. |
| 5,034,228 A | * 7/1991 | Meybeck et al. |
| 5,126,261 A | * 6/1992 | Morris et al. |
| 5,441,740 A | 8/1995 | Ozlen |

FOREIGN PATENT DOCUMENTS

| DE | 43 28 871 | 3/1995 |
| EP | 0 500 332 | 8/1992 |
| FR | 2 756 565 | 6/1998 |
| WO | WO 90/06102 | 6/1990 |

OTHER PUBLICATIONS

H. Murase et al, "Antioxidant and Emulsifying Activity of N–(Long–chain–acyl) histidine and N–(Long–chain–acyl) carnosine", J. Agric. Food Chem. vol. 41, pp. 1601–1604, 1993.

T. Tsunoda et al, "Stability of all–trans–retinol in cream", J. Soc. Cosmet. Chem. vol. 46, pp. 191–198, Jul./Aug. 1995.

A. E. Vasil'ev et al, "Devivativesof Hemin Ligand–Exchange chromatography of Hemin and its Derivatives. Simple Synthesis of Hemin Amides with Amino Acids", J. of Organ. Chem. USSR (English translation) vol. 14, pp. 786–793, 1978.

* cited by examiner

*Primary Examiner*—Thurman K. Page
*Assistant Examiner*—Humera N. Sheikh
(74) *Attorney, Agent, or Firm*—Oblon, Spivak, McClelland, Maier & Neustadt, P.C.

(57) ABSTRACT

A composition containing at least one retinoid and at least one histidine derivative. The histidine derivative improves the stability of the retinoid in the composition. The composition may be used to treat skin and/or hair.

40 Claims, No Drawings

COMBINATION OF A RETINOID WITH A HISTIDINE DERIVATIVE

BACKGROUND OF THE INVENTION

Field of the Invention

The present invention relates to novel cosmetic and/or dermatological compositions, in particular compositions intended for skincare and comprising at least one compound of the retinoid family. More particularly, the invention relates to stable compositions comprising at least one compound of the retinoid family and at least one histidine derivative.

Description of the Background

Cosmetic and/or dermatological compositions based on retinoids have undergone considerable development in recent years. Among the retinoids, the use of retinoic acid in compositions for treating acne is well known.

However, it has been recognized that other derivatives of the retinoid family offer an advantage, both for treating acne and for skincare, in particular for limiting, or even eliminating, the effects of ageing on the skin: wrinkles, a weatherbeaten appearance, yellowing, the loss of elasticity, redness, dryness and the appearance of marks are the usual manifestations of ageing of the skin. These manifestations are proportionately more pronounced when the skin has been frequently exposed to the sun or is particularly sensitive to exposure to UV radiation.

Thus, the effects of intrinsic ageing of the skin (associated with age) and of light-induced ageing (due to exposure to the sun) can be cumulative. The manifestations of ageing usually appear at an advanced age; however, their prevention should be undertaken from the start of adult life, by means of appropriate care measures.

Treatment of the skin with derivatives of the retinoid family forms a part of these preventive or curative measures for caring for the manifestations of ageing, namely: wrinkles, weatherbeaten skin, yellowing, loss of elasticity, redness, dryness and marks.

Among the derivatives of the retinoid family, retinol, also known as vitamin A, and esterified derivatives of retinol are most particularly advantageous. In point of fact, retinol is a natural endogenous constituent of the human body. It is well tolerated when applied to the skin, up to levels much higher than those for retinoic acid. Retinol esters are converted into retinol by the human body.

However, when they are introduced into a cosmetic or dermatological composition intended for topical application, retinol and its esters rapidly degrade, under the effect of light, oxygen, metal ions, oxidizing agents, water or, in particular, under the effect of an increase in temperature. The thermal degradation of retinol was the subject of a study published in J. Soc. Cosm. Chem. 46, 191–198 (July–August 1995).

Various combinations of retinol or of other derivatives of the retinoid family with antioxidants are known, the retinoids being of improved stability in these combinations:

WO 93/00085 describes W/O emulsions comprising retinol and a stabilizing system consisting of a chelating agent such as, for example, EDTA, and an antioxidant which can be either a liposoluble antioxidant, for instance butyl hydroxytoluene (BHT) or vitamin E, or a water-soluble antioxidant, for instance vitamin C. According to this publication, W/O emulsions containing retinol stabilized with a system consisting of a liposoluble antioxidant and a water-soluble antioxidant can also be prepared.

EP 608,433 describes compositions containing retinol and a stabilizer chosen from chelating agents and polysaccharides, oils with an iodine number of greater than 70, polyethylene (propylene) glycols, hydroxycarboxylic acid salts, neutral amino acid salts, liposoluble antioxidants combined with EDTA and a benzophenone, liposoluble antioxidants combined with an acidic compound and a benzophenone, cyclodextrin derivatives in which an antioxidant or a UV screening agent is included, butanediol and/or liposoluble antioxidants, water-soluble benzophenone derivatives, basic amino acids and their salts, acidic amino acids and their salts, polar oils and hydrophilic mineral clays.

Lastly, the use of N-acyl carnosine and histidine derivatives as antioxidants, in particular as inhibitors of the formation of lipid peroxides, in the presence of which retinol is known to be unstable, is known from EP 500,332 and from the publication "Antioxidant and Emulsifying Activity of N-(long-chain-acyl) histidine and N-(long-chain-acyl) carnosine", Hironobu Murase, J. Agric. Food Chem., Vol. 41, 1993, pp. 1601–1604.

However, none of these compounds whether they are described as antioxidants or more specifically as retinoid stabilizers, allow satisfactory stabilization of retinoids to be obtained. Accordingly, there remains a need for compositions containing retinoids which are stabilized from thermal degradation.

SUMMARY OF THE INVENTION

An object of the present invention is to provide compositions containing one or more retinoids, in which the retinoids have enhanced resistance to thermal degradation.

It is another object of the present invention to provide methods of enhancing the resistance of retinoids to thermal degradation.

The inventors have now discovered, surprisingly, that the combination of a retinoid chosen from vitamin A (or retinol) and bioconvertible precursors of vitamin A, with certain histidine derivatives, makes it possible to avoid the degradation, in particular the thermal degradation, of these retinoids. Thus, these retinoids can be introduced into cosmetic and/or dermatological compositions and can be stored for several months, without their efficiency being degraded.

Accordingly, the objects of the present invention, and others, may be accomplished with a composition containing:

(a) at least one retinoid chosen from: vitamin A (or retinol), retinal and bioconvertible precursors of vitamin A, and (b) at least one histidine derivative represented by formula (I) below:

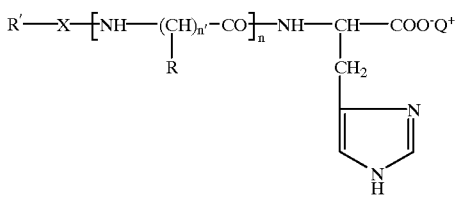

(I)

wherein
  n is an integer ranging from 0 to 5,
  n' is an integer ranging from 1 to 16,
  R represents a side chain of an amino acid,
  X represents a radical chosen from the radicals of formulae, read from left to right:
    —CO—, —O—CO—, —NH—CO—, —SO2—, —NH—CO—CO—, —O—CO—CO—,
  R' represents a linear or branched, saturated or unsaturated, optionally hydroxylated, C6 to C22 alkyl radical or C6 to C22 aminoalkyl radical, the amine function optionally being protected in the form of acetamide or substituted with one or two lower alkyl groups, with the proviso that R' is an aminoalkyl radical as defined above when X=—CO—
  $Q^+$ represents $H^+$ or an organic or inorganic cation,
  as well as the addition salts of a compound of formula (I) with an organic or inorganic acid.

The term vitamin A means retinol of all-trans type or of 13-cis type.

The expression "bioconvertible precursor of vitamin A" denotes any compound which can be converted into vitamin A by the human body. Among these compounds, mention may be made of retinol esters, in particular $C_1$–$C_6$ esters which are very rapidly degraded into retinol by the human body. Among the retinol esters, retinyl acetate and retinyl propionate are more particularly intended.

A subject of the invention is also a cosmetic or dermatological composition comprising the combination as described above and at least one physiologically acceptable support.

A subject of the invention is also the use of at least one histidine derivative of formula (I), as defined above, for improving the stability of a composition comprising a retinoid chosen from vitamin A (or retinol), retinal and bioconvertible precursors of vitamin A.

A subject of the invention is also a process for improving the stability of a composition comprising a retinoid chosen from vitamin A (or retinol), retinal and bioconvertible precursors of vitamin A, this process consisting in combining an effective amount of at least one histidine derivative of formula (I), as defined above, with the said retinoid.

The expression "effective amount of histidine derivative of formula (I)" means an amount which is sufficient to obtain an appreciable and significant improvement in the thermal stability of the retinoid(s) contained in the composition. This minimum amount of stabilizer to be used, which can vary depending on the nature of the physiologically acceptable support selected for the composition, can be determined without difficulty by means of a test for measuring thermal stability, such as the one given in the examples below.

Thus, another subject of the invention is the use of the combination of at least one retinoid chosen from vitamin A (or retinol), retinal and bioconvertible precursors of vitamin A and of at least one histidine derivative of formula (I), in, or for the preparation of, a composition intended for dermatological treatment for controlling and/or preventing irritation, inflammation, immunosuppression and/or acne.

A subject of the invention is also a cosmetic treatment process which consists in controlling the signs of ageing, particularly the signs of ageing induced by photoperoxidation, in particular the photoperoxidation of squalene and/or collagen, by topical application to the skin and/or the scalp and/or the hair of a composition comprising at least one retinoid chosen from vitamin A (or retinol), retinal and bioconvertible precursors of vitamin A, and at least one histidine derivative of formula (I) according to the invention. A subject of the invention is also the use of such a cosmetic composition for controlling and/or preventing the signs of light-induced ageing of the skin and/or the hair. A subject of the invention is also a dermatological composition comprising a combination according to the invention, which is intended for controlling the signs of ageing of the skin or the hair, particularly the signs of ageing induced by photoperoxidation, in particular the photoperoxidation of squalene and/or collagen.

A more complete appreciation of the invention and many of the attendant advantages thereof will be readily obtained as the same becomes better understood by reference to the following detailed description.

DETAILED DESCRIPTION OF THE INVENTION

The pH of the composition according to the invention is preferably greater than or equal to 6, preferably greater than or equal to 7. The pH of the composition according to the invention is generally less than or equal to 12, preferably less than or equal to 10. These pH ranges include all specific values and subranges therebetween, including pH 6.5, 7.0, 7.5, 8.0, 8.5, 9.0, 9.5, 10.0, 10.5, 11.0 and 11.5.

The organic cation ($Q^+$) of the histidine derivatives of formula (I) may be chosen from ammoniums containing a residue chosen from basic amino acids such as lysine or arginine, or alternatively from amino alcohols such as glucamine, N-methylglucamine or 3-amino-1,2-propanediol.

The inorganic cation ($Q^+$) may be chosen from alkali metal or alkaline-earth metal salts such as $Na^+$ or $K^+$, or can be the $NH_4^+$ ion.

The addition salts with an acid may be chosen, for example, from the hydrochlorides, hydrobromides, sulphates, tartrates and acetates.

The compounds of formula (I) include at least one asymmetric carbon in their structure: the invention relates equally to the compounds of D configuration, of L configuration and to mixtures thereof, in particular the racemic mixture of the D and L compounds.

The preferred compounds of formula (I) have at least one of the following characteristics:
  R' preferably denotes a linear or branched, saturated alkyl radical containing from 8 to 18 carbon atoms,
  n is an integer from 1 to 5, and
  n' is an integer ranging from 1 to 11.

Among the linear or branched alkyl radicals containing from 6 to 22 carbon atoms, preferable examples include hexyl, octyl, nonyl, 2-ethylhexyl, dodecyl, hexadecyl and octadecyl radicals.

The lower alkyl groups generally comprise from 1 to 6 carbon atoms. Lower alkyl groups which may be mentioned are methyl, ethyl, propyl, isopropyl, tert-butyl and hexyl radicals.

Among the linear alkyl radicals containing from 6 to 22 carbon atoms which may be mentioned in particular are octyl, dodecyl, hexadecyl and octadecyl radicals.

Among the branched alkyl radicals containing from 6 to 22 carbon atoms, mention may be made in particular of 2-methylpentyl, 1-methylhexyl and 3-methylheptyl radicals.

The expression "unsaturated alkyl radical" preferably refers to a linear or branched radical containing from 6 to 22 carbon atoms comprising one or more double bonds.

The amino acid side chains correspond to the side chains of any of the natural amino acids. Thus, R can in particular represent hydrogen or a methyl or isopropyl radical. These can thus be non-polar side chains, polar but uncharged side chains and negatively or positively charged side chains.

An exemplary process for preparing the compounds of formula (I) comprises the step which consists in reacting with histidine, in an inert solvent, a compound of formula (II)

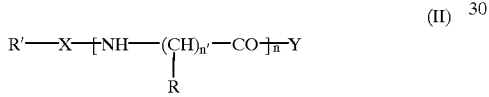
(II)

in which n', n, R, R' and X have the same meanings as in formula (I) above, and Y is a conventional activating group for the acid function.

The reactions for activating acid groups —COOH are well known to those skilled in the art. See for example, to "Advanced Organic Chemistry, Jerry March, 3rd Edition, 1985, pp. 370–377", incorporated herein by reference. The term "coupling agent" refers to any compound capable of substituting the OH group in the compound of formula (IV), and then of subsequently being substituted with the amino acid which it is desired to graft, for example histidine. Coupling agents are described in "Advanced Organic Chemistry, J. March, 3rd Edition, 1985, page 372", incorporated herein by reference. 2-(5-Norbornene-2,3-dicarboximido)-1,1,3,3-tetramethyluronium tetrafluoroborate can be used in particular as a coupling agent.

The starting histidine comprising an asymmetric carbon is used in pure optical form or as a mixture (D; L; D,L) depending on the desired optical form of the compound of formula (I).

Dichloromethane, 1,2-dichloroethane, 1,1,1-trichloroethane, chloroform, acetonitrile, toluene, dioxane, tetrahydrofuran, 1,2-dimethoxyethane, cyclohexane, dimethylformamide, water or a mixture of these solvents can be used as solvent.

The reaction is carried out at a temperature preferably of between −10° C. and +40° C. and more preferably of between 20° C. and 30° C.

The reaction can be carried out in the presence of a base. This can be chosen from alkali metal or alkaline-earth metal hydroxides, sodium hydrogen carbonate, alkali metal alkoxides, alkaline hydrides, tertiary amines such as pyridine, diisopropylethylamine or triethylamine. Sodium hydrogen carbonate is preferably used.

The preferred compounds corresponding to the general formula (I) are those which are chosen from the following formulae:

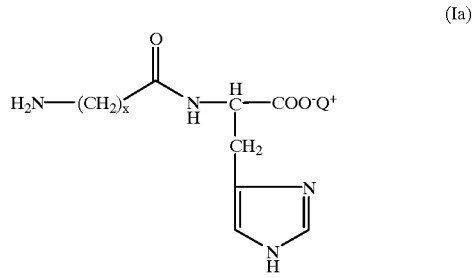
(Ia)

wherein
x is an integer ranging from 6 to 22 and $Q^+$ being as defined above, and

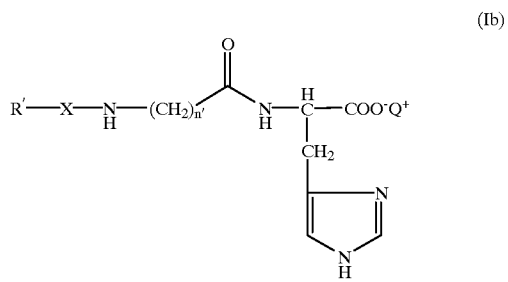
(Ib)

wherein
R', X, $Q^+$ and n' are as described above.

The compounds of formula (Ia) are as described in French patent application serial No. 98/03150 filed on Mar. 13, 1998, incorporated herein by reference.

The compounds of formula (Ib) are in particular as described in French patent application Ser. No. 96/14880 filed on Dec. 4, 1998, and incorporated herein by reference.

The compounds of formula (Ia) are obtained by a process which consists in reacting with histidine, in an inert solvent, a compound of formula (II)

in which n has the same meaning as in formula (I) above, R" represents a protecting group for the amine function, the acid function of the compound (II) being activated, for example in the presence of a coupling agent.

The compounds of formula (Ib), when X represents —O—CO—, are obtained by a process which consists in reacting, in an inert solvent, a compound of formula (II)

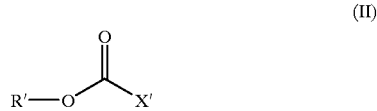
(II)

X' representing a halogen atom, in particular a chlorine atom, or a radical derived from an azole, in particular a radical obtained from an imidazole such as that of formula (III):

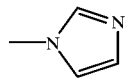

(III)

and R' having the same meaning indicated in formula (Ib) above, either (A) with carnosine, or (B), in a first step, with an amino acid of formula:

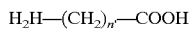

to form a compound of formula (IV) below:

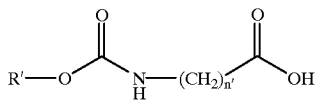

(IV)

R' and n' having the same meanings as those given in formula (I) defined above, and, in a second step, in reacting histidine with the compound of formula (IV), in the presence of a coupling agent.

Examples of preferred compounds corresponding to the general formula (I) include:

N-octyloxycarbonyl-β-alanyl-L-histidine (compound 1),

N-dodecyloxycarbonyl-β-alanyl-L-histidine (compound 2),

N-(12-amino-1-oxododecyl)-L-histidine (compound 3),

N-2-ethylhexyloxycarbonyl-β-alanyl-L-histidine hydrochloride,

N-hexadecyloxycarbonyl-β-alanyl-L-histidine,

N-octylaminocarbonyl-β-alanyl-L-histidine,

N-dodecylaminocarbonyl-β-alanyl-L-histidine,

N-dodecylsulphonyl-β-alanyl-L-histidine,

N-dodecylamino-oxalyl-β-alanyl-L-histidine.

One skilled in the art will be able, by means of simple tests, to adapt the relative proportion of retinoid and of histidine derivatives of formula (I) to obtain the desired effect. The optimum proportions of the various constituents can vary, for example as a function of the molecular weight of the polymer, the content of amines and/or the content of tertiary amines in this polymer.

Besides the retinoid and the histidine derivative of formula (I), the composition according to the invention preferably comprises at least one sunscreen. The addition of a sunscreen makes it possible to reinforce the stability of the combination of the retinoid with the polyamino polymer, by limiting the harmful action of UV on the retinoid. Such a constituent can be chosen from the known families of hydrophilic or lypophilic sunscreens which are active in the UVA and/or UVB range. Mention may be made, for example, of: cinnamic derivatives such as, for example, 2-ethylhexyl p-methoxycinnamate, salicylic derivatives such as, for example, 2-ethylhexyl salicylate and homomenthyl salicylate, camphor derivatives such as, for example, 3-(4-methylbenzylidene)camphor, triazine derivatives such as 2,4,6-tris[p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, β,β-diphenylacrylate derivatives such as 2-ethylhexyl α-cyano-β,β-diphenylacrylate, p-aminobenzoic acid derivatives such as, for example, octyl para-dimethylaminobenzoate, menthyl anthranilate, the screening polymers and screening silicones described in WO 93/04665, incorporated herein by reference, and hydrophilic screening agents containing at least one sulphonic radical —SO$_3$H, such as, for example, 2-phenylbenzimidazole-5-sulphonic acid or benzene-1,4-bis (3-methylidene-10-camphorsulphonic acid).

Another compound known as a retinol stabilizer can also be incorporated into the inventive composition. Examples of these compounds include chelating agents, and polysaccharides, oils with an iodine number of greater than or equal to 70, polyethylene glycols and/or polypropylene glycols, hydroxycarboxylates, amino acids and their salts, antioxidants such as butyl hydroxytoluene, butyl hydroxyanisole, α, β, γ and δ-tocopherols, nordihydrogaiaretine, propyl gallate, fatty acid esters of vitamin C, ascorbic acid, ascorbic acid salts, isoascorbic acid, isoascorbic acid salts, sorbic acid, sorbic acid salts, butanediol, fatty acid esters of pentaerythritol, fatty esters of trimethylolpropane and hydrophilic mineral clays. Such compounds are known as retinoid stabilizers, see EP-A-608,433, incorporated herein by reference.

In the specific case of the treatment of acne, at least one specific antiacne, antiseborrhoeic and/or antibacterial agent, and in particular piroctone olamine sold under the name Octopirox by Hoechst, can also advantageously be incorporated into the composition.

In the compositions according to the invention, the retinoid is preferably introduced in an amount ranging from 0.0001 to 10% by weight relative to the total weight of the composition, advantageously from 0.001 to 3% and even more preferably from 0.01 to 1%. These weight % ranges include all specific values and subranges therebetween, such as 0.1, 0.2, 0.5, 2, 3, 5 and 8% by weight.

In the compositions according to the invention, the histidine derivative of formula (I) is preferably introduced in an amount ranging from 0.001 to 20% by weight relative to the total weight of the composition, advantageously from 0.05 to 10%. These weight % ranges include all specific values and subranges therebetween, such as 0.01, 0.1, 0.5, 1, 2, 5, 15 and 18% by weight.

The compositions of the invention can also comprise cosmetic or dermatological adjuvants chosen from fatty substances, organic solvents, emulsifiers, nonionic thickeners, softeners, antioxidants, opacifiers, stabilizers, silicones, antifoaming agents, moisturizers, vitamins, fragrances, preserving agents, surfactants, preferably nonionic surfactants, fillers, sequestering agents, polymers other than those described above, propellants, acidifying or basifying agents, dyes or any other ingredient commonly used in cosmetics.

The fatty substances can consist of an oil or a wax or a mixture thereof, petroleum jelly, paraffin, lanolin, hydrogenated lanolin or acetylated lanolin; they also comprise fatty acids, fatty alcohols such as lauryl alcohol, cetyl alcohol, myristyl alcohol, stearyl alcohol, palmityl alcohol or oleyl alcohol, as well as 2-octyldodecanol, fatty acid esters such as glyceryl monostearate, polyethylene glycol monostearate, isopropyl myristate, isopropyl adipate, isopropyl palmitate, octyl palmitate, benzoates of $C_{12}$–$C_{15}$ fatty alcohols (Finsolv TN from Finetex), myristyl alcohol polyoxypropylenated with 3 mol of propylene oxide (Witconol APM from Witco), and triglycerides of $C_6$–$C_{18}$ fatty acids such as caprylic/capric acid triglycerides.

Among the oils which can be used in the present invention, mention may be made of mink oil, turtle oil, soybean oil, grapeseed oil, sesame oil, corn oil, rapeseed oil, sunflower oil, cottonseed oil, avocado oil, olive oil, castor oil, jojoba oil, groundnut oil, hydrocarbon oils such as liquid paraffins, squalene and petroleum jelly; esters such as isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate and glyceryl triisostearate; silicone oils such as polymethylsiloxanes, polymethylphenylsiloxanes, polysiloxanes modified with fatty acids, polysiloxanes modified with fatty alcohols, polysiloxanes modified with polyoxyalkylenes, and fluorosilicones; perfluoro and/or organofluorine oils; higher fatty acids such as myristic acid, capric acid, caprylic acid, palmitic acid, stearic acid, behenic acid, oleic acid, linoleic acid, linolenic acid and isostearic acid, and higher fatty alcohols such as cetanol, stearyl alcohol and oleyl alcohol.

The waxes may be animal, plant, mineral or synthetic waxes. Among the animal waxes, mention may be made in particular of beeswaxes and whale wax. Among the plant waxes, mention may be made, inter alia, of carnauba wax, candelilla wax, ouricury wax, cork fibre waxes, sugarcane waxes and Japan waxes. Among the mineral waxes, mention may be made, in particular, of paraffin waxes, lanolin, microcrystalline waxes, lignite waxes and ozokerites. Among the synthetic waxes, mention may be made, in particular, of polyethylene waxes and the waxes obtained by Fisher-Tropsch synthesis. All these waxes are well known to those skilled in the art.

Among the organic solvents, mention may be made of lower alcohols and polyols such as ethanol, isopropanol, propylene glycol, glycerol and sorbitol.

The thickeners, which are preferably nonionic, can be chosen from modified or unmodified guar gums and cellulose gums, such as hydroxypropyl guar gum, cetylhydroxyethylcellulose, silicas such as, for example, Bentone Gel MiO sold by NL Industries or Veegum Ultra sold by Polyplastic.

Of course one skilled in the art will take care to select the optional complementary compound(s) and/or the amounts thereof such that the advantageous properties intrinsically associated with the composition in accordance with the invention are not, or are not substantially, adversely affected by the addition(s) envisaged.

The compositions according to the invention can be in the form of a lotion, a gel, a water-in-oil emulsion, an oil-in-water emulsion or a triple emulsion. They can also be in a vectorized form such as, for example, in the form of nanocapsules, liposomes, nanoemulsions or oleosomes.

These compositions may be used for application to the skin of the body, in particular to the skin of the face and the hands, to mucous and semi-mucous membranes or to the hair.

Such compositions can be in the form of care products or make-up products. In particular, they can be in the form of a care cream, a milk, a tonic, a cleansing and/or make-up-removing product, a mask, an erasing product, an exfoliant, a sunscreen product, a foundation, a tinted cream or a lipstick.

Having generally described this invention, a further understanding can be obtained by reference to certain specific examples which are provided herein for purposes of illustration only and are not intended to be limiting unless otherwise specified.

EXAMPLES

In these examples and counterexamples, the percentages are given by weight of constituent relative to the volume of solvent (W/V), except where otherwise mentioned.

Example 1

Stability test:

The stability of a retinoid is defined in accordance with the present invention by the percentage of the retinoid which remains in its original form after the composition comprising it has been stored for a given period and at a given temperature.

Tests:

Test of stability of 0.3% all-trans retinol in a water/ethanol mixture stored at 45° C.

The conditions of the study are as follows:

test compound at 0.1% (as weight/volume) in water/ethanol (40/60%)

all-trans retinol sold by the company Fluka at 0.3% (as weight/volume) in water/ethanol (40/60%)

aerobic medium with 55% by volume of air and 45% by volume of ethanol/water storage at 45° C. in amber-coloured bottles.

Degradation of the retinol under these conditions reaches 100% in 7 days of storage at 45° C. The storage conditions to which we subjected the compositions are particularly harsh.

The following compositions are tested:

retinol alone at pH 8 and 11 (formulations A and B respectively), retinol with carnosine at pH 8.2 (comparative formulation C), retinol with compound 1 at pH 5.5 and 8.2 (formulations D and E respectively), retinol with compound 2 at pH 12 (formulation F), retinol with compound 3 at pH 8.2 and 12 (formulations G and H respectively), retinol with compound 4 at pH 8.2 and 11 (formulations I and J respectively, compound 4 is N-(5-amino-1-oxopentyl)-L-histidine).

The residual retinol content is monitored by HPLC (on a Spherisorb ODS1 C18 column, by elution with an $H_2O$/$CH_3CO_2H$/$CH_3CO_2NH_4$/acetonitrile mixture: 15/1/0.4/83.6) at 7 days (RT1) and 15 days (RT2) of storage at 45° C. in aerobic medium (55% by volume of air).

The following results are obtained:

| Formulation | RT1 | RT2 |
|---|---|---|
| Formulation A | 0% | 0% |
| Formulation B | 0% | 0% |
| Formulation C | 17% | 4% |
| Formulation D | 0% | 0% |
| Formulation E | 78% | 63% |
| Formulation F | 44% | 10% |
| Formulation G | 78% | 55% |
| Formulation H | 70% | 53% |
| Formulation I | 2% | 0% |
| Formulation J | 69% | 20% |

Thus, it is observed that, for a comparable pH, carnosine stabilizes retinol much less than the histidine derivatives used according to the invention.

Example 2

Compositions according to the invention are prepared as described below with compounds 1, 2, 3 and 4 as compounds of formula (I).

| CTFA name | Formulation 1 |
|---|---|
| Cetyl alcohol | 5% |
| Glyceryl stearate | 3% |
| PEG-50 stearate | 3% |
| Mineral oil | 18.4% |
| Caprylic/capric triglycerides | 5% |
| Fluka all-trans retinol | 0.1% |
| Water | qs 100% |
| Compound of formula (I) | 0.5% |

Obviously, numerous modifications and variations of the present invention are possible in light of the above teachings. It is to be understood that within the scope of the appended claims, the invention may be practiced otherwise than as specifically described herein.

This application is based on French Patent Application Serial No. 98-06603, filed on May 26, 1998, and incorporated herein by reference in its entirety.

What is claimed is:

1. A composition, comprising:
   (a) at least one retinoid selected from the group consisting of vitamin A, retinal and bioconvertible precursors of vitamin A, and
   (b) at least one histidine compound represented by the formula (I):

$$R'-X-[NH-(CH)_{n'}-CO]_n-NH-CH-COO^-Q^+ \quad (I)$$
(with side chain $R$ on the $(CH)_{n'}$ unit, and $CH_2$-imidazole on the terminal CH)

wherein:
n is an integer from 0 to 5;
n' is an integer from 1 to 16;

R represents a side chain of a natural amino acid;
X represents —CO—, —O—CO—, —NH—CO—, —SO$_2$—, —NH—CO—CO— or —O—CO—CO—;
R' represents a linear or branched, saturated or unsaturated, optionally hydroxylated, C6 to C22 alkyl radical or C6 to C22 aminoalkyl radical, wherein the amine function of the aminoalkyl radical is optionally protected in the form of acetamide or is substituted with one or two lower alkyl groups;
with the proviso that R' is an aminoalkyl radical as defined above when X represents —CO—; and
Q$^+$ represents H$^+$ or an organic or inorganic cation; or an addition salt thereof.

2. The composition of claim 1, wherein the retinoid is an all-trans retinol or a 13-cis retinol.

3. The composition of claim 1, wherein the retinoid is selected from the group consisting of $C_1$–$C_6$ retinol esters.

4. The composition of claim 1, having a pH greater than or equal to 6.

5. The composition of claim 1, having a pH greater than or equal to 7.

6. The composition of claim 1, wherein the histidine compound represented by the formula (I) has at least one of the following characteristics:
   i) R' represents a linear or branched, saturated alkyl radical containing from 8 to 18 carbon atoms,
   ii) n is an integer from 1 to 5, or
   iii) n' is an integer from 1 to 11.

7. The composition of claim 1, wherein the histidine compound represented by the formula (I) is represented by the formula (Ia) or (Ib):

$$H_2N-(CH_2)_x-C(=O)-NH-CH(CH_2\text{-imidazole})-COO^-Q^+ \quad (Ia)$$

wherein
x is an integer from 6 to 22, and Q$^+$ is as defined in claim 1, and $$R'-X-NH-(CH_2)_{n'}-NH-CH(CH_2\text{-imidazole})-COO^-Q^+ \quad (Ib)$$

wherein
R', X, Q$^+$ and n' are as defined in claim 1.

8. The composition of claim 1, wherein (b) is selected from the group consisting of N-octyloxycarbonyl-β-alanyl-L-histidine,
N-dodecyloxycarbonyl-β-alanyl-L-histidine,
N-(12-amino-1-oxododecyl)-L-histidine,
N-2-ethylhexyloxycarbonyl-β-alanyl-L-histidine hydrochloride,
N-hexadecyloxycarbonyl-β-alanyl-L-histidine,
N-octylaminocarbonyl-β-alanyl-L-histidine,
N-dodecylaminocarbonyl-β-alanyl-L-histidine,
N-dodecylsulphonyl-β-alanyl-L-histidine, and
N-dodecylamino-oxalyl-β-alanyl-L-histidine.

9. The composition of claim 1, wherein X represents —O—CO—, —NH—CO—, —SO$_2$—, —NH—CO—CO— or —O—CO—CO—.

10. The composition of claim 1, wherein said amino acid side chain R comprises —H, —CH$_3$ or —C$_2$H$_5$.

11. The composition of claim 3, wherein said C$_1$–C$_6$ retinol esters are selected from the group consisting of retinol acetate and retinol propionate.

12. The composition of claim 1, further comprising at least one sunscreen.

13. The composition of claim 1, wherein Q$^+$ is an organic cation, which is an organic ammonium cation.

14. The composition of claim 13, wherein the ammonium cation is based on lysine or arginine.

15. The composition of claim 1, wherein Q$^+$ is an organic cation, which is an amino alcohol cation.

16. The composition of claim 15, wherein the amino alcohol cation is based on glucamine, N-methylglucamine or 3-amino-1,2-propanediol.

17. The composition of claim 1, wherein Q$^+$ is an inorganic cation, which is K$^+$, Na+ or NH$_4^+$.

18. The composition of claim 1, wherein said compound (b) contains at least one asymmetric carbon, whereby a compound of D-configuration, or L-configuration, or a racemic mixture is present.

19. The composition of claim 1, wherein said addition salt is of an inorganic or organic acid.

20. A cosmetic or dermatological composition, or both, comprising the composition of claim 1, and a physiologically acceptable carrier.

21. The composition of claim 20, which contains 0.0001 to 10% by weight of the retinoid.

22. The composition of claim 20, which contains 0.001 to 3% by weight of the retinoid.

23. The composition of claim 20, which contains 0.01 to 1% by weight of the retinoid.

24. The composition of claim 20, which contains 0.001 to 20% by weight of (b).

25. The composition of claim 20, which contains 0.05 to 10% by weight of (b).

26. The composition of claim 20, further comprising at least one compound comprising chelating agents, polysaccharides, oils with an iodine number of greater than or equal to 70, polyethylene glycols or polypropylene glycols, or both, hydroxycarboxylates, amino acids and salts thereof, and antioxidants.

27. The composition of claim 20, further comprising at least one antiacne, antiseborrhoeic or antibacterial agent or combination thereof.

28. The composition of claim 20, which is in the form of a lotion, a gel, a water-in-oil emulsion, an oil-in-water emulsion, a triple emulsion, nanocapsules, liposomes, nanoemulsions, or oleosomes.

29. The composition of claim 20, which is storage-stable.

30. The composition of claim 20, which is in the form of a care cream, a milk, tonic, a cleansing or make-up-removing product, or both, a mask, an erasing product, an exfoliant, a sunscreen product, a foundation, a tinted cream, or a lipstick.

31. A method of making the composition of claim 1, comprising combining (a) and (b).

32. A method of making the composition of claim 1, comprising combining (a), (b) and the physiologically acceptable carrier.

33. A method of treating skin or hair, or both, comprising applying the composition of claim 1, to the skin or hair or both.

34. A method of controlling or preventing irritation, or both, inflammation, immunosuppression or acne on skin or hair or a combination thereof, comprising applying an effective amount of the composition of claim 1, to skin or hair or both.

35. A method of controlling or preventing irritation, or both, inflammation, immunosuppression or acne on skin or hair, or a combination thereof, comprising applying an effective amount of the composition of claim 20, to skin or hair or both.

36. A method of ameliorating the signs of ageing, comprising applying an effective amount of the composition of claim 1, to skin or scalp or hair or a combination thereof.

37. A method of ameliorating the signs of ageing, comprising applying an effective amount of the composition of claim 20, to skin or scalp or hair or a combination thereof.

38. A method of ameliorating the signs of light-induced ageing of the skin or hair, comprising applying an effective amount of the composition of claim 1, to skin or hair or a combination thereof.

39. A method of ameliorating the signs of light-induced ageing of skin or hair, or both, comprising applying an effective amount of the composition of claim 20, to the skin or hair or both.

40. A method of stabilizing retinoids against thermal degradation, comprising combining:
(a) at least one retinoid selected from the group consisting of vitamin A, retinal and bioconvertible precursors of vitamin A, and
(b) at least one histidine compound represented by the formula (I):

$$R'-X-[NH-(CH)_{n'}(R)-CO]_n-NH-CH(CH_2-\text{imidazole})-COO^-Q^+ \quad (I)$$

wherein
n is an integer from 0 to 5,
n' is an integer from 1 to 16,
R represents a side chain of an amino acid,
X represents —CO—, —O—CO—, —NH—CO—, —SO$_2$—, —NH—CO—CO— or —O—CO—CO—, R' represents a linear or branched, saturated or unsaturated, optionally hydroxylated, C6 to C22 alkyl radical or C6 to C22 aminoalkyl radical, wherein the amine function of the aminoalkyl radical is optionally protected in the form of acetamide or is substituted with one or two lower allyl groups, with the proviso that R' is an aminoalkyl radical as defined above when X represents —CO—, $Q^+$ represents $H^+$ or an organic or inorganic cation, or an addition salt thereof.

* * * * *

UNITED STATES PATENT AND TRADEMARK OFFICE
CERTIFICATE OF CORRECTION

PATENT NO. : 6,358,514 B1
DATED : March 19, 2002
INVENTOR(S) : Boudiaf Boussouira et al.

It is certified that error appears in the above-identified patent and that said Letters Patent is hereby corrected as shown below:

<u>Column 12,</u>
Line 1, "a natural amino" should read -- an amino --.

Signed and Sealed this

Eleventh Day of June, 2002

*Attest:*

*Attesting Officer*

JAMES E. ROGAN
*Director of the United States Patent and Trademark Office*